US009056066B2

(12) United States Patent
Ishimaru et al.

(10) Patent No.: US 9,056,066 B2
(45) **Date of Patent: *Jun. 16, 2015**

(54) AGENT FOR SUPPRESSING ELEVATION OF BLOOD GIP LEVEL, AGENT FOR SUPPRESSING ELEVATION OF BLOOD INSULIN LEVEL, AGENT FOR LOWERING BLOOD TRIGLYCERIDE LEVEL AFTER MEAL INGESTION, AND AGENT FOR SUPPRESSING ELEVATION OF BLOOD GLUCOSE LEVEL

(75) Inventors: Kotomi Ishimaru, Tokyo (JP); Kazuhisa Sawada, Ichikai-machi (JP); Noriko Osaki, Utsunomiya (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/996,261

(22) PCT Filed: Dec. 20, 2011

(86) PCT No.: PCT/JP2011/079475

§ 371 (c)(1), (2), (4) Date: Jun. 20, 2013

(87) PCT Pub. No.: WO2012/096108

PCT Pub. Date: Jul. 19, 2012

(65) Prior Publication Data

US 2013/0281367 A1 Oct. 24, 2013

(30) Foreign Application Priority Data

Jan. 12, 2011 (JP) ................................ 2011-004313
Jan. 12, 2011 (JP) ................................ 2011-004314
Jan. 12, 2011 (JP) ................................ 2011-004315
Jan. 12, 2011 (JP) ................................ 2011-004316

(51) Int. Cl.
*A61K 31/785* (2006.01)
*A61K 38/00* (2006.01)
*A23L 1/305* (2006.01)
*C08G 69/10* (2006.01)

(52) U.S. Cl.
CPC ................ *A61K 38/00* (2013.01); *A23L 1/305* (2013.01); *A23V 2002/00* (2013.01); *A61K 31/785* (2013.01); *C08G 69/10* (2013.01)

(58) Field of Classification Search
CPC ..... A61K 38/168; A61K 38/16; A61K 38/02; A23J 3/16; C07K 14/435; A23V 2200/328
See application file for complete search history.

(56) References Cited

U.S. PATENT DOCUMENTS 4,232,007 A 11/1980 Kajihara et al.
6,251,422 B1 6/2001 Tanimoto et al.
6,669,971 B1 12/2003 Kato et al.
8,828,935 B2 9/2014 Ishimaru et al.
8,853,153 B2 10/2014 Ishimaru et al.
8,933,025 B2 1/2015 Ishimaru et al.
2003/0157107 A1 8/2003 Miyawaki et al.
2006/0178343 A1 8/2006 Shimotoyodome et al.
2006/0257468 A1 11/2006 Ho et al.
2007/0099827 A1* 5/2007 Uotani et al. .................. 514/12
2010/0022014 A1 1/2010 Shimotoyodome et al.
2012/0108506 A1 5/2012 Ishimaru et al.
2012/0115779 A1 5/2012 Ishimaru et al.
2012/0122772 A1 5/2012 Ishimaru et al.

FOREIGN PATENT DOCUMENTS

JP 03-030648 A 2/1991
JP 03-047087 A 2/1991
JP 03-290170 A 12/1991
JP 05-095767 A 4/1993
JP 05-186356 A 7/1993
JP 09-028309 A 2/1997
JP 2004-269458 A 9/2004
JP 2005-035957 A 2/2005
JP 2005-200330 A 7/2005
JP 2006-213598 A 8/2006
JP 2006-316022 A 11/2006
JP 2007-022982 A 2/2007
JP 2008-145136 A 6/2008
JP 2008-255063 A 10/2008
JP 2009-096748 A 5/2009
JP 2009-173634 A 8/2009
JP 2010-270062 A 12/2010
JP 2011-020962 A 2/2011
JP 2011-037842 A 2/2011
JP 2011-037843 A 2/2011

(Continued)

OTHER PUBLICATIONS

Ho et al. "g-Polyglutamic Acid Produced by *Bacillus subtilis* (natto): Structural Characteristics", Chemical Properties and Biological Functionalities, Journal of the Chinese Chemical Society, 2006, pp. 1363-1384.*
International Search Report (ISR) for PCT/JP2011/079475; I.A. fd: Dec. 20, 2011, mailed Feb. 14, 2012 from the Japanese Patent Office, Tokyo, Japan.
International Preliminary Report on Patentability (IPRP), Chapter I of the Patent Cooperation Treaty, including the Written Opinion for PCT/JP2011/079475; I.A. fd: Dec. 20, 2013, issued Jul. 16, 2013, by the International Bureau of WIPO, Geneva, Switzerland.
Brown, JC et al., "Preparation of highly active enterogastrone," Can J Physiol Pharmacol 47(1): 113-114, (Jan. 1969), National Research Council of Canada, Ottawa, Canada.
Consensus Statement: "Postprandial Blood Glucose," American Diabetes Association, (DM Nathan et al., Consensus Panel), Diabetes Care 24: 775-778, (Apr. 2001), American Diabetes Association, Alexandria, VA.

(Continued)

*Primary Examiner* — Karlheinz R Skowronek
*Assistant Examiner* — Lianko Garyu
(74) *Attorney, Agent, or Firm* — Sterne, Kessler, Goldstein & Fox P.L.L.C.

(57) ABSTRACT

An agent for suppressing elevation of blood GIP level, an agent for suppressing elevation of blood insulin level, an agent for lowering blood triglyceride level after meal ingestion and an agent for suppressing elevation of blood glucose level, these agents containing potassium polyglutamates as active ingredients.

10 Claims, No Drawings

(56) References Cited

FOREIGN PATENT DOCUMENTS

| | | | |
|---|---|---|---|
| JP | 2011-046647 | A | 3/2011 |
| WO | WO 01/87341 | A1 | 11/2001 |
| WO | WO 2005/049050 | A1 | 6/2005 |
| WO | WO 2007/043606 | | 4/2007 |
| WO | WO 2009/035173 | A1 | 3/2009 |

OTHER PUBLICATIONS

DECODE Study Group, the European Diabetes Epidemiology Group, "Glucose tolerance and cardiovascular mortality: comparison of fasting and 2-hour diagnostic criteria," Arch Intern Med 161(3): 397-405, (Feb. 2001), American Medical Assn, Chicago, IL.

Ellis, PR et al., "The effect of high-molecular-weight guar gum on net apparent glucose absorption and net apparent insulin and gastric inhibitory polypeptide production in the, growing pig: relationship to rheological changes in jejunal digesta," Br J Nutr 74(4): 539-556, (Oct. 1995), Cambridge University Press, Cambridge, UK.

Falko JM et al., "Gastric Inhibitory Polypeptide (GIP) Stimulated by Fat Ingestion in Man," J Clin Endocrinol Metab 41: 260-265, (Aug. 1975), Endocrine Society, Chevy Chase, MD.

Fukase, N et al., "Effects of AO-128, α-glacosidase inhibitor on secretion of gasric inhibitory polypeptide and truncated glucagon-like peptide-1," (machine translated as: "Effect to give to secretion of GastricInhibitoryPolypeptide (GIP) of one alpha GlucosideaseInhibitor (AO-128) and TruncatedGlucagon-likePeptide-1 (tGLP-1)"), Clin Report 25(15): 103-109, (Dec. 1991), Medical*Online.

Gatenby, SJ et al., "Effect of partially depolymerized guar gum on acute metabolic variables in patients with non-insulin-dependent diabetes," Diabet Med 13(4): 358-364, (Apr. 1996), Wiley, Sussex, England.

Miyawaki, K et al., "Inhibition of gastric inhibitory polypeptide signaling prevents obesity," Nat Med 8(7): 738-742, (Jul. 2002), Nature Publishing Company, New York, NY.

Modan, M et al., "Hyperinsulinemia. A link between hypertension obesity and glucose intolerance," J Clin Invest 75(3): 809-817, (Mar. 1985), American Society for Clinical Investigation, Ann Arbor, MI.

Morgan, LM et al., "The effect of soluble- and insoluble-fibre supplementation on post-prandial glucose tolerance, insulin and gastric inhibitory polypeptide secretion in healthy subjects," Br J Nutr 64(1): 103-110, (Jul. 1990), Cambridge University Press, Cambridge, UK.

Morgan, LM et al., "The effect of guar gum on carbohydrate-, fat- and protein-stimulated gut hormone secretion: modification of postprandial gastric inhibitory polypeptide and gastrin responses," Br J Nutr 53(3): 467-475, (May 1985), Cambridge University Press, Cambridge, UK.

Nunes, CS et al., "Glucose absorption, hormonal release and hepatic metabolisdm after guar gum ingestion," Reprod Nutr Dev 32: 11-20 (1992), Elsevier, Paris, France.

Oda, T et al., eds., Chapter 3-2: "Alimentary tract, a function and clinical condition," in "Gastrointestinal Tract, Function and Pathological Condition," pp. 201-218, 1981, Chugai Igakusha, Japan.

Polonsky, KS et al., "Twenty-four-hour profiles and pulsatile patterns of insulin secretion in normal and obese subjects," J Clin Invest 81(2): 442-448, (Feb. 1988), American Society for Clinical Investigation, Ann Arbor, MI.

Requejo, F et al., "Effects of alpha-glucosidase inhibition and viscous fibre on diabetic control and postprandial gut hormone responses," Diabet Med 7(6): 515-520, (Jul. 1990), Wiley, Sussex, England.

Risso, A et al., "Intermittent high glucose enhances apoptosis in human umbilical vein endothelial cells in culture," Am J Physiol Endocrinol Metab 281: E924-E930, (Nov. 2001), American Physiological Society, Bethesda, MD.

Tominaga, M et al., "Impaired glucose tolerance is a risk factor for cardiovascular disease, but not impaired fasting glucose, The Funagata Diabetes Study," Diabetes Care 22: 920-924 (Jun. 1999), American Diabetes Association, Alexandria VA.

Excerpted file history of U.S. Appl. No. 13/383,665: Amendment and Reply filed Jul. 29, 2014, The United States Patent and Trademark Office, Alexandria, VA.

Excerpted English Translation of the Notice of Reasons for Rejection, for JP Patent Application No. 2010-161231, mailed Jun. 24, 2014, by the Japanese Patent Office, Tokyo, Japan.

Grundy, SM et al., "Effectiveness and tolerability of simvastatin plus fenofibrate for combined hyperlipidemia (the SAFARI trial)," Am J Cardiol, Feb. 2005; 95(4):462-468, Excerpta Medica, New York, NY.

Excerpted file history of U.S. Appl. No. 13/383,633: USPTO Office action mailed Oct. 4, 2013 by The United States Patent and Trademark Office, Alexandria, VA; and Applicants' Amendment and Reply filed Dec. 4, 2013.

Excerpted file history of U.S. Appl. No. 13/383,658: USPTO Office action mailed Sep. 27, 2013 for U.S. Appl. No. 13/383,658, The United States Patent and Trademark Office, Alexandria, VA; and Applicants' Amendment and Reply filed Dec. 2, 2013.

Excerpted file history of U.S. Appl. No. 13/383,665: USPTO Office action mailed Dec. 9, 2013 for U.S. Appl. No. 13/383,665, The United States Patent and Trademark Office, Alexandria, VA.

Reiser, S et al., "Serum insulin and glucose in hyperinsulinemic subjects fed three different levels of sucrose," Am J Soc Clin Nutr, Nov. 1981; 34: 2348-2358, Am Soc Clin Nutr, Bethesda, MD.

Guagnano, MT et al., "Large waist circumference and risk of hypertension," International Journal of Obesity, Sep. 2001; 25(9): 1360-1364, Nature Publishing Group, London, England.

Houpt, KA et al., "The pig as a model for the study of obesity and of control of food intake: A review," Yale J Biol Med 52:307-329 (1979), Yale Journal of Biology and Medicine, New Haven, CT.

Ishikawa, H. et al., "Preparation and characterization of liposomal microencapsulated poly-γ-glutamic acid for prevention of Ca-phosphate precipitation under intestinal environment," Food Sci Technol Res 10:227-231 (2004), Japanese Society for Food Science and Technology, Tsubuka, Japan.

Sung, MH et al., "Natural and edible biopolymer poly-gamma-glutamic acid: synthesis, production, and applications," Chem Rec, Jan. 2005; 5(6): 352-366, Wiley, New York, NY.

Yacowitz, H et al., "Effects of oral calcium upon serum lipids in man," British Medical J 1: 1352-1354 (May 1965), British Medical Association, London, England.

U.S. Appl. No. 13/383,633 final Office action mailed Feb. 19, 2014 by The United States Patent and Trademark Office, Alexandria, VA.

U.S. Appl. No. 13/383,658, final Office action mailed Feb. 21, 2014, The United States Patent and Trademark Office, Alexandria, VA.

U.S. Appl. No. 13/383,665, Applicants' Reply filed Feb. 20, 2014 to the Dec. 9, 2013 Office action from The United States Patent and Trademark Office, Alexandria, VA.

Karmaker, S et al., "Amelioration of hyperglycemia and metabolic syndromes in type 2 diabetic $KKA^y$ mice by poly(γ-glutamic acid)oxovanadium(IV) complex," ChemMedChem, Nov. 2007; 2(11): 1607-1612, Wiley-VCH Verlag GmbH & Co., Weinheim, Germany.

Karmaker, S. et al., "Antidiabetic Activity of the Orally Effective Vanadyl-Poly (-Glutamic Acid) Complex in Streptozotocin(STZ)-induced Type 1 Diabetic Mice," J Biomater Appl, 22: 449-464 (Mar. 2008), SAGE Publications, Los Angeles, CA.

Wei Liang et al., eds., "Diabetes," p. 4, Inner Mongolia Science and Technology Press, China, Oct. 31, 2002.

Extended European search report for EP Application No. 10799921.1, (corresponding to U.S. Appl. No. 13/383,633) including the supplementary European search report and the European search opinion, mailed Dec. 5, 2012, the European Patent Office, Munich, Germany.

Notification of First Office Action for Chinese Patent Application No. 201080031436.7, (corresponding to U.S. Appl. No. 13/383,633) mailed Sep. 20, 2012, Patent Office of the People's Republic of China, Beijing, China.

International Search Report (ISR) for PCT/JP2010/062050, I.A. fd: Jul. 16, 2010, (corresponding to U.S. Appl. No. 13/383,633), mailed Sep. 14, 2010, from the Japanese Patent Office, Tokyo, Japan.

International Preliminary Report on Patentability (Chapter I of the Patent Cooperation Treaty) for PCT/JP2010/062050, I.A. fd: Jul. 16,

(56) References Cited

OTHER PUBLICATIONS 2010, (corresponding to U.S. Appl. No. 13/383,633) , issued Feb. 7, 2012, from the Internation Bureau of WIPO, Genera, Switzerland.
Notification of First Office Action for Chinese Patent Application No. 201080031941.1, (corresponding to U.S. Appl. No. 13/383,658) , mailed Sep. 20, 2012, Patent Office of the People's Republic of China, Beijing, China.
Extended European search report for EP 10799922.9, (corresponding to U.S. Appl. No. 13/383,658) , including the supplementary European search report and the European search opinion, dated Feb. 5, 2013, European Patent Office, Munich, Germany.
International Search Report (ISR) for PCT/JP2010/062051, I.A. fd: Jul. 16, 2010, (corresponding to U.S. Appl. No. 13/383,658) , mailed Sep. 14, 2010, from the Japanese Patent Office, Tokyo, Japan.
International Preliminary Report on Patentability (Chapter I of the Patent Cooperation Treaty) for PCT/JP2010/062051, I.A. fd: Jul. 16, 2010, (corresponding to U.S. Appl. No. 13/383,658), issued Feb. 7, 2012, from the International Bureau of WIPO, Genera, Switzerland.
Notification of First Office Action for CN Patent Application No. 201080031674.8, (corresponding to U.S. Appl. No. 13/383,665), mailed Sep. 10, 2012, from the Patent Office of the People's Republic of China, Beijing, China.
Extended European search report for EP application No. 10799923.7, (corresponding to U.S. Appl. No. 13/383,665), including the supplementary European search report and the European search opnion, dated Dec. 3, 2012, European Patent Office, Munich, Germany.
International Search Report (ISR) for PCT/JP2010/062052, I.A. fd: Jul. 16, 2010, (corresponding to U.S. Appl. No. 13/383,665), mailed Sep. 14, 2010, from the Japanese Patent Office, Tokyo, Japan.
International Preliminary Report on Patentabiltiy (Chapter I of the Patent Cooperation Treaty) for PCT/JP2010/062052, I.A. fd: Jul. 16, 2010, (corresponding to U.S. Appl. No. 13/383,665), issued Feb. 7, 2012, from the International Bureau of WIPO, Genera, Switzerland.
Excerpted file history of U.S. Appl. No. 13/383,633: Applicants' May 12, 2014 Amendment and Reply to the USPTO final Office action mailed Feb. 19, 2014, and Applicant-Initiated Interview Summary for interview of Apr. 30, 2014, posted May 1, 2014.
Excerpted file history of U.S. Appl. No. 13/383,658: Applicants' May 14, 2014 Amendment and Reply to the final Office action mailed Feb. 21, 2014, by The United States Patent and Trademark Office, Alexandria, VA.
Excerpted file history of U.S. Appl. No. 13/383,633: Notice of Allowance mailed Jun. 17, 2014 and Examiner initiated interview summary posted Jun. 17, 2014, The United States Patent and Trademark Office, Alexandria, VA.
Excerpted file history of U.S. Appl. No. 13/383,658: Notice of Allowance mailed Jun. 6, 2014 and Examiner initiated interview summary posted Jun. 6, 2014, The United States Patent and Trademark Office, Alexandria, VA.
Excerpted file history of U.S. Appl. No. 13/383,665: Office action mailed May 22, 2014, The United States Patent and Trademark Office, Alexandria, VA.
Kiuchi, K, "Miso & Natto," Food Culture, 2001, No. 3, pp. 7-10 and cover page, Kikkoman Institute for International Food Culture, Noda-City, Chiba, Japan.
Food Culture, 2001, No. 3, cover page and pp. 2-3, Kikkoman Institute for International Food Culture, Noda-City, Chiba, Japan.
Bastyr, EJ et al., "Therapy focused on lowering postprandial glucose, not fasting glucose, may be superior for lowering $HbA_{1c}$. IOEZ Study Group," Diabetes Care, Sep. 2000; 23: 1236-1241, Am. Diabetes Assoc, Alexandria, VA.
Taniguchi, A et al., "Natto and viscous vegetables in a Japanese style meal suppress postprandial glucose and insulin responses," Asia Pac J Clin Nutr, Jan. 2008; 17(4): 663-668, HEC Press, Melbourne, Australia.
Yamaguchi, F. et al., "Detection of γ-polyglutamic acid (γ-PGA) by SDS-PAGE," Biosci Biotech Biochem 60(2):255-258 (1996), Japan Society for Bioscience, Biotechnology, and Agrochemistry, Komiyama Printing Co., Ltd., Japan.
Excerpted file history of U.S. Appl. No. 13/383,665: Notice of Allowance and Issue Fee(s) Due, mailed Sep. 23, 2014, The United States Patent and Trademark Office, Alexandria, VA.
Yamada, Nobuhiro et al., "Ti jian zhi hou zi wo gai shan gan you san zhi yu dan gu chun," ["Self-Improvement After Medical Checks: Triglyceride and Cholesterol,"], Shenyang : Lianoning ke xue ji shu, China, 2008, p. 34.
Zhang, Zhixiong, ed., "Physiology," Feb. 28, 2009, Chinese Medicine Press, Publisher, China, p. 267.
"Notification of the Second Office Action," for Chinese Patent Application No. 201180064932.7, mailed Dec. 31, 2014, Patent Office of the People's Republic of China, Beijing, China.

* cited by examiner

AGENT FOR SUPPRESSING ELEVATION OF BLOOD GIP LEVEL, AGENT FOR SUPPRESSING ELEVATION OF BLOOD INSULIN LEVEL, AGENT FOR LOWERING BLOOD TRIGLYCERIDE LEVEL AFTER MEAL INGESTION, AND AGENT FOR SUPPRESSING ELEVATION OF BLOOD GLUCOSE LEVEL

FIELD OF THE INVENTION

The present invention relates to an agent for suppressing elevation of blood GIP level, an agent for suppressing elevation of blood insulin level, an agent for lowering blood triglyceride level after meal ingestion, and an agent for suppressing elevation of blood glucose level.

BACKGROUND OF THE INVENTION

GIP (gastric inhibitory polypeptide or glucose-dependent insulinotrophic polypeptide) is one of the gastrointestinal hormones, and is secreted from K-cells present in the small intestine during meal ingestion. It is known that GIP functions as a suppressor of gastric-acid secretion and suppressor of gastric motility (see Patent Literatures 1 to 3).

It is also known that GIP promotes secretion of insulin from pancreatic β-cells and accelerates glucose uptake into adipocytes in the presence of insulin. It is therefore considered that the functions of GIP contribute to obesity. In fact, it was reported that obesity is suppressed when GIP functions are inhibited (see Non-patent Literature 4).

Furthermore, it was reported that GIP contributes to insulin resistance (see Non-patent Literature 4). When insulin resistance develops, the effect of insulin on sugar uptake decreases. As a result, hyperinsulinemia occurs. It is said that hyperinsulinemia is a fundamental cause leading to development of various lifestyle diseases such as obesity. Thus, it is important to prevent or reduce insulin resistance also from the viewpoint of decreasing the risk of lifestyle diseases.

Hence, effects such as promotion of digestion, reduction of upset stomach, and prevention or reduction of obesity and insulin resistance can be expected if GIP can be effectively suppressed.

Previous studies show that 3-bromo-5-methyl-2-phenylpyrazolo[1,5-a]pyrimidin-7-ol (BMPP) and pyrazolopyrimidine compounds are substances capable of inhibiting the functions of GIP. Furthermore, guar gum and the like are known as substances capable of suppressing postprandial secretion of GIP (see Patent Literatures 1 and 2, and Non-patent Literatures 5 to 10). However, these substances have not been found to be sufficient from the viewpoints of safety and efficacy.

Insulin is one of the peptide hormones secreted from pancreatic β-cells in the pancreas, and functions to decrease elevated blood glucose level and maintain it at a normal level. The main physiological effects of insulin include promotion of uptake of sugars, amino acids and the like, and promotion of protein synthesis in the muscle tissue; promotion of sugar uptake and utilization thereof, promotion of lipid synthesis, suppression of fat decomposition and burning, and promotion of protein synthesis in the adipose tissue; and the like.

Secretion of insulin is promoted mainly by glucose. When blood sugar level (blood glucose level) elevates owing to introduction of sugar into the body such as after a meal, insulin is secreted so as to decrease the elevated blood sugar level. As a result, the blood insulin level elevates. The secretion of insulin is therefore very important for preventing diabetes mellitus by keeping blood sugar level constant.

However, it is known that continuous secretion of insulin under hyperglycemic condition leads to insulin resistance in the skeletal muscles, liver and adipose tissue that are target organs of insulin. When insulin resistance occurs, a larger amount of insulin is secreted from the pancreas so as to compensate for insufficient blood sugar reduction effect. When such an excess secretion of insulin is repeated, the pancreas gets exhausted, and finally the ability of the pancreatic β-cells to secrete insulin declines, while the high insulin resistance in the target organs is maintained. The above functional deterioration of the regulatory mechanism of insulin in the body leads to constitutional predispositions susceptible to development of lifestyle diseases such as diabetes mellitus, and as a result, obesity, Type II diabetes mellitus (hypertension) and the like are apt to develop (see Non-patent Literature 11).

Until recently, it has been considered that the amount of insulin secreted into the blood varies with blood sugar level, i.e., amount of carbohydrates ingested. But, in recent years, it was newly reported that fat uptake, as well as carbohydrate uptake, is also correlated with the elevation of blood insulin level (see Patent Literature 3). According to Patent Literature 3, it was confirmed that ingestion of carbohydrate together with fat induces excessive secretion of insulin beyond the level induced by ingesting carbohydrates alone. Further, it was also ascertained that the excessive secretion of insulin due to such simultaneous ingestion of carbohydrate and fat is a factor highly correlated to obesity.

Meanwhile, it was reported that hyperglycemia and hyperlipidemia are independent, risk factors for cardiovascular events (Non-Patent Literatures 12 and 13). In addition, it was reported regarding hyperglycemia that fasting hyperglycemia has a low correlation with the probability of death caused by circulatory diseases, whereas blood sugar level has a high correlation with the probability of death caused by circulatory diseases in patients with hyperglycemia having a 2-hour value of 200 mg/dL or more in the glucose tolerance test (OGTT) (Non-Patent Literature 13). It was further reported that in the case where vascular endothelial cells are cultured in a hyperglycemic state, apoptosis of the cells occurs with higher frequency when exposed to an intermittent hyperglycemic condition than when exposed to a continuous hyperglycemic condition (Non-Patent Literature 14).

Further, as compared to healthy people, insulin secretion is lower in diabetes mellitus type 1 patients and insulin secretion in the early postprandial period is lower in diabetes mellitus type 2 patients. The postprandial blood sugar level of healthy people is regulated by insulin, and in general, does not rise above 7.8 mmol/L (140 mg/dL) in response to eating, and generally returns to the level before meal ingestion within 2 to 3 hours (Non-Patent Literatures 15 and 16). In contrast, in type 1 and type 2 diabetic patients with decreased insulin functions, postprandial hyperglycemia is observed with extremely high frequency. Further, postprandial hyperglycemia is a phenomenon which appears before clinically obvious diabetes mellitus with a progressive decrease in insulin function and the β cell activity (a decrease in insulin secretion). It is therefore believed that the prevention of postprandial hyperglycemia leads to the prevention of diabetes mellitus and arteriosclerosis.

From such standpoint, administration of α-glucosidase inhibitors which delay the digestion and absorption of carbohydrates in the small intestine, administration of sulfonium urea formulations which promote insulin secretion, rapidacting insulin secretagogues and the like are performed in order to reduce postprandial hyperglycemia.

The α-glucosidase inhibitors, however, have problems in that the effect cannot be exerted unless the inhibitors are administered before intake of carbohydrates; the inhibitors do not affect the elevation of blood glucose level caused by intake of glucose which is a monosaccharide; and intestinal symptoms such as diarrhea and gas retention caused by abnormal fermentation of sugars in the colon occur. In addition, the sulfonium urea formulations cannot exert the effect unless the formulations are administered before intake of carbohydrates, and when the formulations are administered excessively, excessive secretion of insulin is induced, to thereby cause hypoglycemia, so that caution is required. Further, these synthetic medical formulations cannot be easily obtained because prescriptions are required. In addition, the formulations may cause various adverse effects, and for the use thereof, strict supervision and guidance by doctors are required.

A triglyceride is a kind of neutral fat, and most neutral fats contained in blood are triglycerides. It is known that hypertriglyceridemia and hyperlipidemia develop with continuance of a high triglyceride level in the blood. Hyperlipidemia is considered to be a cause of arteriosclerosis, and act as the initial trigger for inducing disorders such as cardiac disease and cerebral vascular disease.

In general, since changes in blood triglyceride level are strongly affected by diet, complete regulation of blood triglyceride level using only medicaments is said to be difficult. A stronger focus has therefore been placed on the quality of ingested dietary fat than on medical therapy. For example, lowering blood triglyceride level by eating highly-unsaturated fatty acids, such as linoleic acid and linolenic acid, has been recommended. But, since excessive consumption of the highly-unsaturated fatty acids induces production of overoxidized fatty acids in vivo, the possibility of inducing various lifestyle related diseases has been pointed out.

From the viewpoint of the above circumstances, there is a need to suppress elevation of blood triglyceride level by a safer means which does not induce adverse effects even if involving administration or consumption on a daily basis. Recent years, as substances which suppress elevation of blood triglyceride level safely and effectively, xanthane gum, propylene glycol alginate ester (see Patent literature 4), chitosan (see Patent literature 5) and a processed starch (see Patent literature 6) have been reported as fat absorption suppressors.

Due to their high water retaining ability, polyglutamic acids are widely used as moisturizing agents, absorbing agents and the like in the fields of foods, medical treatment, cosmetics and the like, and have attracted attention as highly safe biodegradable polymers. It was reported that polyglutamic acids have an effect of promoting calcium absorption through the small intestine and an effect of suppressing elevation of blood pressure (for example, see Patent Literatures 7 and 8). In addition, an agent for reducing blood sugar level using polyglutamic acids has been suggested for suppressing elevation of blood sugar level (see Patent Literature 9). Further, it was reported that polyglutamic acids have an effect of suppressing the absorption of neutral fat, and can be used for the treatment, reduction and suppression of development of hypertriglyceridemia (see Patent Literature 10).

But no pharmaceutical effects of specific salts of polyglutamic acids have been reported so far.

CITATION LIST

Patent Literatures

Patent Literature 1: WO 01/87341 A

Patent Literature 2: JP-A-2006-213598 ("JP-A" means unexamined published Japanese patent application)

Patent Literature 3: JP-A-2008-145135

Patent Literature 4: JP-A-5-186356

Patent Literature 5: JP-A-3-290170

Patent Literature 6: JP-A-2004-269458

Patent Literature 7: JP-A-5-95767

Patent Literature 8: JP-A-2008-255063

Patent Literature 9: JP-A-2005-200330

Patent Literature 10: JP-A-2009-173634

Non-Patent Literatures

Non-Patent Literature 1: J. C. Brown at al., Canadian J. Physiol. Pharmacol., 47: 113-114, 1969

Non-Patent Literature 2: J. M. Falko at al., J. Clin. Endocrinol. Metab., 41(2): 260-265, 1975

Non-Patent Literature 3: "Gastrointestinal Tract, Function and Pathological Condition", Chugai Igakusha, p. 205-216, 1981

Non-Patent Literature 4: Nat. Med. 8(7): 738-42, 2002

Non-Patent Literature 5: Diabet Med, 13(4): 358-64, 1996

Non-Patent Literature 6: Br. J. Nutr. 74(4): 539-56, 1995

Non-Patent Literature 7: Reprod. Nutr. Dev. 32(1): 11-20, 1992

Non-Patent Literature 8: Br. J. Nutr. 64(1): 103-10, 1990

Non-Patent Literature 9: Diabet Med. 7(6): 515-20, 1990

Non-Patent Literature 10: Br. J. Nutr, 53(3): 467-75, 1985

Non-Patent Literature 11: J. Clin. Invest. 75(3): 809-17, 1985

Non-Patent Literature 12: Diabetes Care. 1999; 22: 920-924

Non-Patent Literature 13: Arch. Intern. Med. 2001; 161: 397-405

Non-Patent Literature 14: Am. J. Physiol. Endocrinol. Metab, 2001; 281: E924-930

Non-Patent Literature 15: Diabetes Care 2001; 24(4): 775-778

Non-Patent Literature 16: J. Clin. Invest. 1988; 81(2): 442-448

SUMMARY OF THE INVENTION

The present invention is contemplated for providing an agent for suppressing elevation of blood GIP level which is useful for medicinal use and application in foods. Specifically, the present invention is contemplated for providing an agent for suppressing elevation of blood GIP level which is useful for medicinal use or non-medicinal application in foods for decreasing the risk of development of, and preventing, reducing, alleviating or treating, upset stomach caused by elevation of blood GIP level after meal ingestion, for promoting digestion, or for decreasing the risk of development of, and preventing, reducing, alleviating or treating, obesity and insulin resistance.

In addition, the present invention is contemplated for providing an agent for suppressing elevation of blood insulin level, which can suppress elevation of blood insulin level after meal ingestion. Further, the present invention is also contemplated for providing an agent for suppressing elevation of blood insulin level, which is useful for preventing or reducing obesity and diabetes mellitus caused by elevation of blood insulin level. Specifically, the present invention is contemplated for providing an agent for suppressing elevation of blood insulin level, which suppresses elevation of blood insulin level after meal ingestion and is thereby useful for medicinal use or non-medicinal application in foods for decreasing the risk of development of, and preventing, reducing, alleviating or treating, obesity and diabetes mellitus.

Moreover, the present invention is contemplated for providing an agent for lowering blood triglyceride level after meal ingestion, which is useful for medicinal use and application in food. Specifically, the present invention is contemplated for providing an agent for lowering blood triglyceride level after meal ingestion, which lowers blood triglyceride level after meal ingestion and is thereby useful for medicinal use or non-medicinal application in foods for decreasing the risk of development of, and preventing, reducing, alleviating or treating, hypertriglyceridemia, hyperlipidemia and arteriosclerosis.

In addition, the present invention is contemplated for providing an agent for suppressing elevation of blood glucose level, which may suppress elevation of blood glucose level after meal ingestion. Further, the present invention is also contemplated for providing an agent for suppressing elevation of blood glucose level, which is useful for preventing or mitigating diabetes mellitus, obesity and arteriosclerosis caused by elevation of blood glucose level. Specifically, the present invention is contemplated for providing an agent for suppressing elevation of blood glucose level, which suppresses elevation of blood glucose level after meal ingestion and is thereby useful for medicinal use or non-medicinal application in foods for decreasing the risk of development of, and preventing, reducing, alleviating or treating, diabetes mellitus, obesity and arteriosclerosis.

The present inventors studied functions of polyglutamic acids and their salts to suppress GIP secretion, and found that potassium polyglutamates markedly suppress GIP secretion after meal ingestion and are particularly useful for promoting digestion, reducing upset stomach, or preventing or reducing obesity and insulin resistance.

Further, the present inventors found that salts of polyglutamic acids have an effect of suppressing elevation of blood GIP level after meal ingestion. The present inventors further found that among the salts of polyglutamic acids, potassium salts have an outstanding effect of suppressing elevation of blood insulin level.

Further, the present inventors found that salts of polyglutamic acids have an effect of suppressing elevation of blood triglyceride level after meal ingestion. The present inventors further found that among the salts of polyglutamic acids, potassium salts have an effect of lowering blood triglyceride level after meal ingestion.

Further, the present inventors found that potassium polyglutamates are excellent in effect of suppressing elevation of blood glucose level.

The present invention was completed based on the above findings.

The present invention provides the following means.

<1> Use of a potassium polyglutamate for the preparation of an agent for suppressing elevation of blood GIP level.

<2> Use of a potassium polyglutamate for the preparation of an agent for suppressing elevation of blood insulin level.

<3> Use of a potassium polyglutamate for the preparation of an agent for lowering blood triglyceride level after meal ingestion.

<4> Use of a potassium polyglutamate for the preparation of an agent for suppressing elevation of blood glucose level.

<5> The use of a potassium polyglutamate according to <1>, wherein the agent for suppressing elevation of blood GIP level is an agent for suppressing elevation of blood GIP level after meal ingestion.

<6> The use of a potassium polyglutamate according to <2>, wherein the agent for suppressing elevation of blood insulin level is an agent for suppressing elevation of blood insulin level after meal ingestion.

<7> The use of a potassium polyglutamate according to <4>, wherein the agent for suppressing elevation of blood glucose level is an agent for suppressing elevation of blood glucose level after meal ingestion.

<8> A potassium polyglutamate for use in the suppression of elevation of blood GIP level.

<9> A potassium polyglutamate for use in the suppression of elevation of blood insulin level.

<10> A potassium polyglutamate for use in the lowering of blood triglyceride level after meal ingestion.

<11> A potassium polyglutamate for use in the suppression of elevation of blood glucose level.

<12> Non-therapeutic use of a potassium polyglutamate for the suppression of elevation of blood GIP level.

<13> Non-therapeutic use of a potassium polyglutamate for the suppression of elevation of blood insulin level.

<14> Non-therapeutic use of a potassium polyglutamate for the lowering of blood triglyceride level after meal ingestion.

<15> Non-therapeutic use of a potassium polyglutamate for the suppression of elevation of blood glucose level.

<16> A method for suppressing elevation of blood GIP level, the method including administering a potassium polyglutamate to a subject.

<17> A method for suppressing elevation of blood insulin level, the method including administering a potassium polyglutamate to a subject.

<18> A method for lowering, blood triglyceride level after meal ingestion, the method including administering a potassium polyglutamate to a subject.

<19> A method for suppressing elevation of blood glucose level, the method including administering a potassium polyglutamate to a subject.

The agent for suppressing elevation of blood GIP level of the present invention can suppress elevation of blood GIP level, specifically elevation of blood GIP level after meal ingestion. Furthermore, the agent for suppressing elevation of blood GIP level of the present invention can suppress elevation of blood GIP level effectively, and is therefore useful for decreasing the risk of development of, and preventing, reducing, alleviating or treating, upset stomach, for promoting digestion and for decreasing the risk of development of, and preventing, reducing, alleviating or treating, obesity and insulin resistance.

The agent for suppressing elevation of blood insulin level of the present invention can suppress elevation of blood insulin level, specifically elevation of blood insulin level after meal ingestion. Furthermore, the agent for suppressing elevation of blood insulin level of the present invention suppresses excessive elevation of blood insulin level and therefore controls the functional mechanisms of insulin in the body after meal ingestion within a normal range, and is thereby useful for preventing or reducing obesity and diabetes mellitus.

The agent for lowering blood triglyceride level after meal ingestion of the present invention can lower blood triglyceride level after meal ingestion. Furthermore, the agent for lowering blood triglyceride level of the present invention controls blood lipid level within a normal range, and is thereby useful for decreasing the risk of development of, and preventing, reducing, alleviating or treating, hypertriglyceridemia and hyperlipidemia, and for decreasing the risk of development of, and preventing, reducing, alleviating or treating, arteriosclerosis.

The agent for suppressing elevation of blood glucose level of the present invention can suppress elevation of glucose level, specifically elevation of blood glucose level after meal ingestion. Furthermore, the agent for suppressing elevation of blood glucose level of the present invention suppresses elevation of blood glucose level after meal ingestion and therefore controls blood glucose level in the body within a normal range, and is thereby useful for decreasing the risk of development of, and preventing, reducing, alleviating or treating, diabetes mellitus, obesity and arteriosclerosis.

Other and further features and advantages of the invention will appear more fully from the following description.

DETAILED DESCRIPTION OF THE INVENTION

Hereinafter, the present invention is described in detail.

The agent for suppressing elevation of blood GIP level, the agent for suppressing elevation of blood insulin level, the agent for lowering blood triglyceride level after meal ingestion, and the agent for suppressing elevation of blood glucose level of the present invention (hereinafter referred to agent of the present invention as a superordinate concept including these agents) contain potassium salts of polyglutamic acids (potassium polyglutamates) as active ingredients. A polyglutamic acid is a compound in which the carboxyl group at the γ-position and the amino group at the α-position of glutamic acids are bound to each other with a peptide bond, and a structural formula thereof is represented by (—NH—CH(COOH)—$CH_2$—$CH_2$—CO—)n. The potassium polyglutamates used in the present invention are compounds represented by the above structural formula except that 50% or more of the hydrogen atoms in the carboxyl groups of the above structural formula are substituted with potassium. The potassium polyglutamates used in the present invention are preferably compounds represented by the above structural formula except that 60% or more, more preferably 70% or more, more preferably 80% or more, more preferably 90% or more, more preferably 95% or more, more preferably 99% or more of the hydrogen atoms in the carboxyl groups of the above structural formula are substituted with potassium. It is further preferable that substantially all of the hydrogen atoms in the carboxyl groups of the above structural formula are substituted with potassium. Further, it is preferable that the carboxyl group positioned at terminal end of the above structural formula is also substituted with potassium.

The potassium polyglutamates have functions of remarkably suppressing elevation of blood GIP level, elevation of blood insulin level, elevation of blood triglyceride level and elevation of blood glucose level, as compared to polyglutamic acids and the other salts of polyglutamic acids. Therefore, the potassium polyglutamates can be used as the agent of the present invention and can also be used for the preparation of the agent of the present invention. It has not been known so far that the potassium polyglutamates have functions of suppressing elevation of blood GIP level, suppressing elevation of blood insulin level, lowering blood triglyceride level after meal ingestion, suppressing elevation of blood glucose level. And also, it has not been known that the potassium polyglutamates have an effect to prevent or reduce obesity and insulin resistance.

The agent for suppressing elevation of blood GIP level of the present invention can be preferably used for suppressing elevation of blood GIP level particularly after meal ingestion. Specifically, the agent can be more preferably used for suppressing elevation of blood GIP level after ingesting a meal containing both fat and carbohydrates, more preferably after ingesting a meal containing a large amount of fat, more preferably after ingesting a triacylglycerol-rich meal.

The triacylglycerol in the meal is not specifically limited. Specific examples of the fatty component containing a large amount of triacylglycerol include butter, lard, fish oil, corn oil, rapeseed oil, olive oil, sesame oil and the like.

The carbohydrate component in the meal is also not specifically limited. Specific examples of the carbohydrate component include cooked rice, starch, wheat flour, sugar, fructose, glucose, glycogen and the like.

An ingestion amounts of the fat and the carbohydrates are not specifically limited as long as these amounts are within ranges included in a normal meal.

In the present invention, "suppression of elevation of blood GIP level" mainly refers to suppression of elevation of blood GIP level that occurs after meal ingestion. The suppression of the elevation of blood GIP level after meal ingestion does not necessarily mean that the elevation of blood GIP level caused after meal ingestion is completely suppressed, and encompasses moderating the degree of elevation of blood GIP level as compared to the case in which the agent for suppressing elevation of blood GIP level of the present invention is not administered. Furthermore, "function (effect) of suppressing elevation of blood GIP level" in the present invention encompasses both a function of suppressing secretion of GIP in which elevation of blood GIP level is suppressed by suppressing GIP secretion from the digestive tract, and a function of lowering GIP in which elevation of blood GIP level is suppressed by lowering the blood GIP level.

In the present invention, "suppressing elevation of blood insulin level" means suppression of elevation of blood insulin level caused by ingesting foods containing primarily fat and carbohydrate.

The suppression of the elevation of blood insulin level after meal ingestion does not necessarily mean that the elevation of blood insulin level caused after meal ingestion is completely suppressed, and encompasses moderating the degree of elevation of blood insulin level as compared to the case in which the agent for suppressing elevation of blood insulin level of the present invention is not administered.

Furthermore, in the present invention, "function (effect) of suppressing elevation of blood insulin level" encompasses both a function of suppressing secretion of insulin in which elevation of blood insulin level is suppressed by suppressing secretion of insulin from the pancreas, and a function of lowering insulin in which elevation of blood insulin level is suppressed by lowering the blood insulin level.

The fat described above is not specifically limited as long as it is fatty component included in a normal meal and capable of promoting insulin secretion. Specific examples include butter, lard, fish oil, corn oil, rapeseed oil, olive oil, sesame oil and the like.

The carbohydrates described above are not specifically limited as long as it is a carbohydrate component that is included in a normal meal and promote secretion of insulin. Specific examples include cooked rice, starch, wheat flour, sugar, fructose, glucose, glycogen and the like.

It is also known that, when the above-mentioned carbohydrates are ingested with fat, the elevation of blood insulin level is enhanced as compared to the case in which carbohydrates are ingested solely. The agent for suppressing elevation of blood insulin level of the present invention can effectively suppress rapid elevation of blood insulin level caused after ingesting both the fat and carbohydrates described above. Thus, for example even when fat and carbohydrates are ingested in an amount of not less than 5 g/60 kg body weight and not less than 10 g/60 kg body weight respectively in a meal, the agent for suppressing elevation of blood insulin level of the present invention can suppress (approach) elevation of blood insulin level to a normal degree of elevation.

As shown in Examples described below, the agent for lowering blood triglyceride level after meal ingestion of the present invention can lower blood triglyceride level after meal ingestion (after ingesting foods, beverages and the like, which contain general carbohydrates, fat, proteins etc).

In the present invention, "suppressing elevation of blood glucose level" mainly means suppression of elevation of blood glucose level after meal ingestion. The suppression of the elevation of blood glucose level after meal ingestion does not necessarily mean that the elevation of blood glucose level caused after meal ingestion is completely suppressed, and encompasses moderating the degree of elevation of blood glucose level as compared to the case in which the agent for suppressing elevation of blood glucose level of the present invention is not administered.

The term "reduction" in the present specification encompasses changing for the better, preventing deterioration, delaying progression, reversal of progression and preventing progression of diseases, symptoms or conditions.

The term "prevention" in the present specification means that the developments of diseases or symptoms in individuals are prevented or delayed, or the risk of development of diseases or symptoms in individuals are lowered.

The molecular weight of the potassium polyglutamates used in the present invention is preferably a weight-average molecular weight of about 500 or more, more preferably of 1,000 or more, more preferably of 2,000 or more, more preferably of 3,000 or more, more preferably of 5,000 or more. Although, the upper limit of the weight-average molecular weight of the potassium polyglutamates used in the present invention is preferably about 5,000,000, it is preferable that the preparation has a comparatively lower viscosity from the viewpoints of preparation, and of feeling of the throat, slimy feeling, easiness of swallowing and the like when the agent for suppressing elevation of blood insulin level of the present invention is used in the form of an oral liquid preparation. Thus, the weight-average molecular weights of the potassium polyglutamates used in the present invention is more preferably 1,000,000 or less, more preferably 500,000 or less.

Although the effect of suppressing elevation of blood GIP level by the potassium polyglutamates is observed in overall potassium polyglutamates regardless of their molecular weight, the potassium polyglutamates having larger molecular weights to some extent are more excellent in an effect of suppressing elevation of blood GIP level.

Thus, the weight-average molecular weight of the potassium polyglutamates used in the present invention is preferably from 500 to 5,000,000, more preferably from 1,000 to 1,000,000, more preferably from 2,000 to 500,000, more preferably from 3,000 to 500,000, more preferably from 4,000 to 400,000, more preferably from 5,000 to 300,000, more preferably from 6,000 to 240,000, in order to more effectively suppress elevation of blood GIP level. The weight-average molecular weight can be measured with, for example, high performance liquid chromatography using a gel filtration column.

Although the effect of suppressing elevation of blood insulin level by the potassium polyglutamates is observed in overall potassium polyglutamates regardless of their molecular weight, the potassium polyglutamates having too large molecular weight tend to show a less effect of suppressing elevation of blood insulin level.

The potassium polyglutamates used in the agent for suppressing elevation of blood insulin level of the present invention show an extremely higher effect of suppressing elevation of blood insulin level as compared to polyglutamic acids and metal salts thereof other than potassium salts which have a weight-average molecular weight similar to the potassium polyglutamates. The weight-average molecular weight of the potassium polyglutamates used in the agent for suppressing elevation of blood insulin level of the present invention is preferably from 500 to 1,000,000. In order to more effectively suppress elevation of blood insulin level, the weight-average molecular weight is more preferably from 1,000 to 800,000, more preferably from 2,000 to 400,000, more preferably from 3000 to 200,000, more preferably from 4,000 to 150,000, more preferably from 5,000 to 50,000, more preferably from 5,000 to 20,000, more preferably from 6,000 to 12,000.

Although the effect of lowering blood triglyceride level after meal ingestion by the potassium polyglutamates is observed in overall potassium polyglutamates regardless of their molecular weight, the potassium polyglutamates having a lower molecular weight tend to show a higher effect.

The weight-average molecular weight of the potassium polyglutamates used in the agent for lowering blood triglyceride level after meal ingestion in the present invention is preferably from 500 to 5,000,000, more preferably from 1,000 to 1,000,000, more preferably from 2,000 to 500,000, more preferably from 3,000 to 500,000, more preferably from 4,000 to 400,000, more preferably from 5,000 to 300,000, more preferably from 6,000 to 240,000.

The effect of suppressing elevation of blood glucose level by the potassium polyglutamates is observed in overall potassium polyglutamates regardless of their molecular weight.

The weight-average molecular weight of the potassium polyglutamates used in the agent for suppressing elevation of blood glucose level of the present invention is preferably from 500 to 5,000,000, more preferably from 1,000 to 1,000,000, more preferably from 2,000 to 500,000, more preferably from 3,000 to 500,000, more preferably from 6,000 to 500,000, more preferably from 8,000 to 400,000, more preferably from 10,000 to 300,000, more preferably from 12,000 to 240,000.

The potassium polyglutamates used in the present invention can be obtained by neutralizing polyglutamic acids or salts thereof produced by chemical synthesis or microorganisms, or commercially available polyglutamic acids or salts thereof, using an aqueous solution of potassium hydroxide as described in Examples described below. Further, the potassium polyglutamates can be also produced by microorganisms cultured in a mixed medium containing potassium. The optical activity of glutamic acids that constitute the potassium polyglutamates may be dextro-rotatory or levo-rotatory, and also may be a mixture thereof. A natural polyglutamic acid is a polymer in which glutamic acids are bound to each other at their γ-position, and examples of wild type microorganisms that produce polyglutamic acids may include a part of bacteria belonging to genus *Bacillus* including *Bacillus subtilis* var. *natto* and related species thereof (*Bacillus subtilis* var. *chungkookjang, Bacillus licheniformis, Bacillus megaterium, Bacillus anthracis, Bacillus halodurans*), *Natrialba aegyptiaca, Hydra* and the like [Ashiuchi, M., et al.: Appl. Microbiol. Biotechnol., 59, pp. 9-14 (2002)]. As examples of the production of polyglutamic acids using a gene recombination technique, it has been known that a recombinant *Bacillus subtilis* ISW1214 strain, which is constructed by gene transfer with a plasmid, produces polyglutamic acids in an amount of about 9 g/L/5 days [Ashiuchi, M., et al.: Biosci. Biotechnol. Biochem., 70, pp. 1794-1797 (2006)], and a recombinant *E. coli*, which is constructed by gene transfer with a plasmid, produces polyglutamic acids in an amount of about 4 g/L/1.5 days [Jiang, H., et al.: Biotechnol. Lett., 28, pp. 1241-1245 (2006)]. Furthermore, polyglutamic acids are commercially produced as food additives, materials for cosmetics and thickening agents, and the like, and it is also possible to purchase polyglutamic acids supplied by domestic or foreign manufacturers of polyglutamic acids (for example, domestic manufacturers: Nippon Poly-Glu Co., Ltd., Ichimaru Pharcos Co., Ltd., Meiji Food Materia Co., Ltd. and the like, foreign manufacturers: BioLeaders Corporation and the like).

The potassium polyglutamates used in the present invention can suppress GIP secretion, insulin secretion, elevation of blood triglyceride level and elevation of blood glucose level, after ingesting carbohydrates, fat and/or proteins. Moreover, the suppression effects are remarkably higher than those of polyglutamic acids and other salts of polyglutamic acids.

The agent of the present invention may be the above described potassium polyglutamates themselves. In addition, the agent of the present invention may contain adequate liquid or solid excipients or expanders, such as titanium oxide, calcium carbonate, distilled water, lactose and starch, in addition to potassium polyglutamates. Although the content of the potassium polyglutamates in the agent of the present invention is not specifically limited, the content is preferably from 0.01 to 100% by mass, more preferably from 0.1 to 95% by mass, further preferably from 1 to 90% by mass, particularly preferably from 5 to 85% by mass.

When the agent of the present invention is used as foods, medicaments or the like, the potassium polyglutamates can be administered alone to humans and animals by gastrointestinal administration, intraperitoneal administration, intravascular administration, intradermal administration, subcutaneous administration or the like, or can be ingested as a form of various foods, medicinal products, pet foods or the like, into which the potassium polyglutamates are blended as active ingredients.

As the foods, in addition to general foods, it is possible to apply to foods such as cosmetic foods, foods for diseased persons and foods for specified health use, which have the concepts of decreasing the risk of development of, and preventing, reducing, alleviating or treating, upset stomach, of enhancing digestion, and of decreasing the risk of development of, and preventing, reducing, alleviating or treating, obesity and insulin resistance, in the case of the agent for suppressing elevation of blood GIP level; the concepts of suppressing elevation of an insulin level in the blood, and of decreasing the risk of development of, and preventing, reducing, alleviating or treating, obesity and diabetes mellitus, in the case of the agent for suppressing elevation of blood insulin level; the concepts of lowering blood triglyceride level after meal ingestion, and of decreasing the risk of development of, and preventing, reducing, alleviating or treating, hypertriglyceridemia, hyperlipidemia and arteriosclerosis, in the case of the agent for lowering blood triglyceride level after meal ingestion; and the concepts of suppressing elevation of blood glucose level, and of decreasing the risk of development of, and preventing, reducing, alleviating or treating, obesity and diabetes mellitus, in the case of the agent for suppressing elevation of blood glucose level, respectively, and indicate those effects as necessary. When used as a medicinal product, the agent can be formed into an oral solid formulation such as a tablet and a granule agent, or an oral liquid formulation such as an oral liquid agent and a syrup agent.

When preparing the oral solid formulation as the agent of the present invention, a tablet, a coated tablet, a granular agent, a powder agent, a capsule agent or the like can be produced by a conventional method after blending an excipient, and if needed, a binder, a disintegrating agent, a lubricating agent, a coloring agent, a taste masking agent, a flavoring agent and the like to a potassium polyglutamates. Alternatively, when preparing the oral liquid formulation, an oral liquid agent, a syrup agent, an elixir agent or the like can be prepared by a conventional method by blending in a taste masking agent, a buffering agent, a stabilizer, a taste masking agent and the like.

Although the content of the potassium polyglutamates in each of the above-mentioned foods and formulations is not specifically limited, the content is preferably from 0.01 to 100% by mass, more preferably from 0.03 to 90% by mass, more preferably from 0.1 to 80% by mass, more preferably from 0.3 to 70% by mass, more preferably from 1 to 60% by mass.

The effective administration (ingestion) amount (dosage) of the potassium polyglutamates in each of the above-mentioned foods and formulations is preferably from 0.001 to 1.0 g/kg body weight per day, more preferably from 0.003 to 0.5 g/kg body weight per day, more preferably from 0.01 to 0.2 g/kg body weight per day.

The agent of the present invention is preferably administered or ingested during or before or after meal ingestion, and can be administered or ingested more preferably during the period from 30 minutes before starting meal ingestion to 30 minutes after finishing the meal ingestion, and more preferably during the period from 10 minutes before starting meal ingestion to 10 minutes after finishing the meal ingestion.

The term "after meal ingestion" in the present specification indicates a period from just after finishing meal ingestion to a time when most of carbohydrates in the meal are absorbed from the intestine. More specifically, it indicates a period from just after finishing meal ingestion (0 min) to 6 hours after finishing the meal ingestion, preferably from just after finishing meal ingestion (0 min) to 5 hours after finishing the meal ingestion, more preferably from just after finishing meal ingestion (0 min) to 4 hours after finishing the meal ingestion, and further preferably from just after finishing meal ingestion (0 min) to 3 hours after finishing the meal ingestion (Diabete Care, 2001, 24 (4): 775-778).

The present invention also provides, as one aspect thereof, use of potassium polyglutamates for the preparation of an agent for suppressing elevation of blood GIP level, of an agent for suppressing elevation of blood insulin level, of an agent for lowering blood triglyceride level after meal ingestion, and of an agent for suppressing elevation of blood glucose level.

Further, the present invention also provides, as another aspect thereof, potassium polyglutamates for use in the suppression of elevation of blood GIP level, in the suppression of elevation of blood insulin level, in the lowering of blood triglyceride level after meal ingestion, and in the suppression of elevation of blood glucose level.

Further, the present invention also provides, as further another aspect thereof, non-therapeutic use of potassium polyglutamates for the suppression of elevation of blood GIP level, for the suppression of elevation of blood insulin level, for the lowering of blood triglyceride level after meal ingestion, and for the suppression of blood glucose level. The "non-therapeutic use" in the present invention may be use in human or non-human animals, or specimens derived therefrom. In addition, the "non-therapeutic" is a concept that does not encompass medical practices, namely, does not encompass treatments for human bodies and non-human animals for the purpose of treatment which are conducted by doctors or medical workers.

Further, the present invention also provides, as further another aspect thereof, a method for suppressing elevation of blood GIP level, a method for suppressing elevation of blood insulin level, a method for lowering blood triglyceride level after meal ingestion, and a method for suppressing elevation of blood glucose level, these methods including administering potassium polyglutamates to a subject.

Although subjects of administration or ingestion of the agent of the present invention are not specifically limited as long as the subjects are in need thereof, obese persons and persons with metabolic syndrome, and potential patients thereof are preferable as the subjects of the administration or ingestion. In Japan, since a recommended standard BMI is 22, subjects having BMI=22 or more are preferable and subjects having BMI=25 or more are more preferable. In Europe and the United States, since BMI of 25 or more is considered to be overweight in a criterion for obesity, subjects having BMI=25 or more are preferable, and subjects having BMI=30 or more are more preferable. In a diagnostic criterion for metabolic syndrome in Japanese, a man having a waist measuring of 85 cm or more or a woman having a waist measuring of 90 cm or more, who meets at least one of the following three criteria falls within a potential patient, or the man or woman who meets at least two of the following criteria falls within metabolic syndrome: (1) blood triglyceride level is 150 mg/dl or more or HDL cholesterol level is less than 40 mg/dL, (2) being hyperglycemia (having a fasting blood sugar level of 110 mg/dL or more), and (3) being hypertension (130/85 mHg or more). Thus, these persons are preferable as the subjects of the administration or ingestion. In the United States, a person who meets three or more of the following criteria: an abdominal girth (102 cm or more for men and 88 cm or more for women), a high neutral fat, a low HDL, hypertension, and a high fasting-blood-sugar, falls within metabolic syndrome. Thus, these persons including persons who meet two or more of the above criteria and fall within a potential patient are preferable as the subjects of the administration or ingestion.

In the case of the agent for suppressing elevation of blood GIP level, it is preferable that subjects of administration or ingestion are persons having a fasting blood glucose level of 100 mg/dL or more, or having fasting blood triglyceride level of 100 mg/dL or more, and/or having fasting blood GIP level of 10 pg/mL or more.

In the case of the agent for suppressing elevation of blood insulin level, it is preferable that subjects of administration or ingestion are persons having fasting blood glucose level of 100 mg/dL or more, or having fasting blood triglyceride level of 100 mg/dL or more.

In the case of the agent for lowering blood triglyceride level after meal ingestion, it is preferable that subjects of administration or ingestion are persons having fasting blood triglyceride level of 100 mg/dL or more.

In the case of the agent for suppressing elevation of blood glucose level, it is preferable that subjects of administration or ingestion are persons having fasting blood glucose level of 100 mg/dL or more, or having fasting blood triglyceride level of 100 mg/dL or more. Further, it is preferable that subjects of administration or ingestion are persons having blood glucose level of 140 mg/dL or more at 2 hours after finishing meal ingestion.

EXAMPLES

Hereinafter, the present invention will be described more in detail with reference to Examples, but the present invention is not limited thereto.

[Analysis Procedures]

Method for Quantifying Potassium Polyglutamate and Method for Determining Weight-Average Molecular Weight of Potassium Polyglutamate—1:

Quantification and weight-average molecular weight determination of potassium polyglutamates were performed by the means of gel permeation with D-6000 HPLC system (manufactured by Hitachi High-Technologies Corporation). The analysis conditions were that TSKGel G4000PWXL and TSKGel G6000PWXL gel permeation columns (trade names, manufactured by Tosoh Corporation) were used as an analytical column, 0.1 M sodium sulfate was used as an eluent, the flow rate was 1.0 mL/min, the column temperature was 50° C. and the wavelength of UV for detection was 210 nm. Concentrations were calibrated by preparing a calibration curve using polyglutamic acids having a molecular weight of 880 k (manufactured by Meiji Food Materia Co., Ltd.). Weight-average molecular weight was measured using polyglutamic acids having various different molecular weights (those manufactured by Wako Pure Chemical Industries, Ltd. (trade name: 162-21411 and 162-21401), SIGMA-ALDRICH (trade name: P-4886 and P-4761) and Meiji Food Materia Co., Ltd. (molecular weight of 880 k)) as standard materials, the weight-average molecular weights of these polyglutamic acids being obtained in advance by using pullulan (trade name: Shodex STANDARD P-82, manufactured by Showa Denko KK).

Method for Determining Weight-Average Molecular Weight of Potassium Polyglutamate—2:

Weight-average molecular weight determination of potassium polyglutamates with low molecular weights having molecular weights of around 10 k was performed by the means of gel permeation with D-6000 HPLC system (manufactured by Hitachi High-Technologies Corporation). The analysis conditions were that TSKGel G3000PWXL permeation columns (trade names, manufactured by Tosoh Corporation) were used as an analytical column, 0.1 M sodium sulfate was used as an eluent, the flow rate was 0.8 mL/min, the column temperature was 50° C. and the wavelength of UV for detection was 210 nm. Weight-average molecular weight was measured using polyglutamic acids (manufactured by Meiji Food Materia Co., Ltd., molecular weight of 9 k) and poly-hydroxyproline (manufactured by SIGMA-ALDRICH, molecular weight of 4 k) as standard materials, the weight-average molecular weights thereof being obtained in advance by using pullulan (trade name: Shodex STANDARD P-82, manufactured by Showa Denko K.K.).

Metal-Analysis Method for Salts of Polyglutamic Acids:

The metal analysis for salts of polyglutamic acids was performed by the means of ion chromatography using D-7000 HPLC system (manufactured by Hitachi High-Technologies Corporation). As the analysis conditions, Shodex IC YK-G as a guard column and Shodex ICYK-421 as an analysis column (both are trade names, manufactured by Showa Denko K.K.) were used, 1.5 mM citric acid aqueous solution was used as an eluent, and detection was carried out at a flow rate of 1.0 mL/min at a column temperature of 40° C. using an electric conductivity detector. A sodium standard solution (1000 ppm) and a potassium standard solution (1000 ppm), manufactured by KANTO CHEMICAL CO., INC., were used as standard samples, and the calibration curves of these standard substances were prepared in a range from 10 to 100 mg/L. The metal analysis for salts of polyglutamic acids was carried out based on these calibration curves.

Preparation Example 1

Preparation of Potassium Polyglutamate Having Weight-Average Molecular Weight of 12,000

Using sodium polyglutamates having weight-average molecular weight of 9,000 (manufactured by Meiji Food Materia Co., Ltd.) as starting materials, 500 mL of 10 (w/w) % aqueous solution thereof was prepared. Then, the pH of this solution was adjusted to 2 or less with hydrochloric acid under ice-cooling. After that, the generated acid precipitate was collected by centrifugation (trade name: himac CR21 GIII, manufactured by Hitachi Koki Co., Ltd.) at 8,000 rpm for 5 minutes. The obtained precipitate was washed with an equal amount of distilled water, and subjected to centrifugation once more. This washing operation was repeated twice, and the obtained precipitate was then suspended in 300 mL of distilled water, followed by neutralization with an aqueous solution of potassium hydroxide to be pH 7 or more. The above-mentioned acid treatment and neutralization treatment with potassium hydroxide were carried out once more, and to the resulting neutralized sample, 2.5 times higher amount of ethanol was added, and the sample was left to stand overnight under ice-cooling. The precipitate generated by the addition of the ethanol was collected by centrifugation (same as above) at 14,000 rpm for 5 minutes, and the collected sample was subjected to drying under reduced pressure to obtain 27.4 g of a solid sample. The weight-average molecular weight of this sample was calculated as 12,000 by the analysis procedures described above. In addition, potassium was detected in an amount equivalent to the amount of the carboxyl groups of polyglutamic acids in this sample, and the amount of sodium was under a detection limit. It was therefore confirmed that substantially all hydrogen atoms of the carboxyl groups were substituted with potassium.

Preparation Example 2

Preparation of Potassium Polyglutamate Having Weight-Average Molecular Weight of 240,000

Using sodium polyglutamates having weight-average molecular weight of 350,000 (manufactured by Meiji Food Materia Co., Ltd.) as starting materials, 1 L of 10 (w/w) % aqueous solution thereof was prepared. Then, the pH of this solution was adjusted to 1 or less with hydrochloric acid under ice-cooling. After that, the generated acid precipitate was collected by centrifugation (trade name: himac CR21 GIII, manufactured by Hitachi Koki Co., Ltd.) at 8.000 rpm for 5 minutes. The obtained precipitate was washed with an equal amount of distilled water, and subjected to centrifugation once more. This washing operation was repeated twice, and the obtained precipitate was then suspended in 800 mL of distilled water, followed by neutralization with an aqueous solution of potassium hydroxide to be pH 7 or more. The above-mentioned acid treatment and neutralization treatment with potassium hydroxide were carried out once more, and the precipitate generated by the addition of ethanol was collected by centrifugation (same as above) at 14,000 rpm for 5 minutes, and the collected sample was subjected to drying under reduced pressure to obtain 36.2 g of a solid sample. The weight-average molecular weight of this sample was calculated as 240,000 by the analysis procedures described above. In addition, potassium was detected in an amount equivalent to the amount of the carboxyl groups of polyglutamic acids in this sample, and the amount of sodium was under a detection limit. It was therefore confirmed that substantially all hydrogen atoms of the carboxyl groups were substituted with potassium.

Preparation Example 3

Preparation of Potassium Polyglutamate Having Weight-Average Molecular Weight of 6,000

Using sodium polyglutamates having weight-average molecular weight of 9,000 (manufactured by Meiji Food Materia Co., Ltd.) as starting materials, 125 mL of 20 (w/w) % aqueous solution thereof was prepared. Then, the pH of this solution was adjusted to 1 or less with hydrochloric acid. After that, this PGA solution was incubated at 95° C. for 12 hours and generated acid precipitate was collected by centrifugation (trade name: himac CR21 GIII, manufactured by Hitachi Koki Co., Ltd.) at 8,000 rpm for 5 minutes. The obtained precipitate was washed with an equal amount of distilled water, and subjected to centrifugation once more. This washing operation was repeated twice, and the obtained precipitate was then suspended in 300 mL of distilled water, followed by neutralization with an aqueous solution of potassium hydroxide to be pH 7 or more. The above-mentioned acid treatment and neutralization treatment by potassium hydroxide were carried out once more, and to the resulting neutralized sample, 2.5 times higher amount of ethanol was added, and the sample was left to stand overnight under ice-cooling. The precipitate generated by the addition of the ethanol was collected by centrifugation (same as above) at 14,000 rpm for 5 minutes, and the collected sample was subjected to drying under reduced pressure to obtain 16.5 g of a solid sample. The weight-average molecular weight of this sample was calculated as 6,000 by the analysis procedures described above. In addition, potassium was detected in an amount equivalent to the amount of the carboxyl groups of polyglutamic acids in this sample, and the amount of sodium was under a detection limit. It was therefore confirmed that substantially all hydrogen atoms of the carboxyl groups were substituted with potassium.

Test Example 1

Pharmacological Function of Potassium Polyglutamate

Samples for oral administration were prepared using potassium polyglutamates with weight-average molecular weights of 12,000 and 240,000 (prepared in Preparation Examples 1 and 2, respectively) and sodium polyglutamates with weight-average molecular weights of 9,000 and 350,000 (manufactured by Meiji Food Materia Co., Ltd.) as described below. In addition, oral administration was carried out using ten 8-week-old male mice (C57BL/6J Jcl: manufactured by CLEA Japan, Inc.) per each group as described below, followed by collecting blood, and blood GIP levels, blood insulin levels, blood triglyceride levels and blood glucose levels were measured by procedures described below.

Test Example 2

Pharmacological Function of Potassium Polyglutamate with Low Molecular Weight Samples for oral administration were prepared using potassium polyglutamates with weight-average molecular weight of 6,000 (prepared in Preparation Example 3), potassium polyglutamates with weight-average molecular weight of 12,000 (prepared in Preparation Example 1), and sodium polyglutamates with weight-average molecular weight of 9,000 (manufactured by Meiji Food Materia Co., Ltd.) as described below. In addition, oral administration was carried out using seven 8-week-old male mice (C57BU6J Jcl: manufactured by CLEA Japan, Inc.) per each group as described below, followed by collecting blood, and blood GIP levels, blood insulin levels, blood triglyceride levels were measured by procedures described below.

Preparation of Samples for Oral Administration:

An emulsion liquid was prepared by emulsifying glucose (manufactured by Kanto Kagaku) and triolein (Glyceryl trioleate: manufactured by Sigma) using lecithin (made from eggs, manufactured by Wako Pure Chemical Industries) and albumin (derived from bovine serum, manufactured by Sigma). A sample for oral administration was prepared by adding the salts of polyglutamic acids to this emulsion liquid so that the final concentrations be 5 (w/w) % of the salts of polyglutamic acids, 5 (w/w) % of glucose, 5 (w/w) % of triolein, and emulsifier (0.2 (w/w) % of lecithin and 1.0 (w/w) % of albumin). A sample in which water had been added instead of the salts of polyglutamic acids was prepared as a control sample.

Oral Administration and Collection of Blood:

The initial blood sampling was conducted from the orbital vein of a mouse that had been food-deprived overnight, using a heparin-treated hematocrit capillary (manufactured by VITREX) under ether anesthesia. Thereafter, the oral administration sample was administered orally by using a feeding needle, and after 10 minutes, 30 minutes, 1 hour and 2 hours, the blood was collected from the orbital vein under ether anesthesia. The amount of oral administration to the mouse is shown in the following Table 1.

TABLE 1

| Amount of oral administration to mouse | | | |
|---|---|---|---|
| | Glucose (mg/1 g body weight) | Triolein (mg/1 g body weight) | Salt of polyglutamic acid (mg/1 g body weight) |
| Control group | 2 | 2 | — |
| Group administered salt of polyglutamic acid | 2 | 2 | 2 |

Measurement and Evaluation of GIP Level in Blood

The blood collected by the heparin-treated hematocrit capillary was stored under ice-cooling until blood plasma separation, and centrifuged at 11,000 rpm for 5 minutes to give blood plasma. Blood GIP level in the obtained plasma was measured by using a Rat/Mouse GIP (Total) ELISA kit (manufactured by Linco Research/Millipore co., ELISA method).

The GIP levels in bloods up to 2 hours after the oral administration of the sample were measured. As a result, it was found that the blood GIP level became the maximum at 10 minutes after the administration. Thus, the difference (Δ value) between the maximum value (at 10 minutes after the administration) and the initial value (at the time of the initial blood collection) of the blood GIP level was defined as the maximum GIP-level elevation, and Table 2 (results of Test Example 1) and Table 3 (results of Test Example 2) show the values when the value obtained from the control group defined as 100.

The statistically-significant difference between the groups was also studied based on the obtained values of the maximum GIP-level elevation, and is shown in Table 2 and Table 3. When significance ($p<0.05$) was recognized by an analysis of variance, verifications were performed between the salts of polyglutamic acids-administered groups and the control group, and between the sodium salts-administered groups and similar molecular weight of the potassium salts-administered groups using a multiple comparison test (Bonferroni/Dunn method). From the obtained result, significance was judged with considering $p<0.05$ as a significant difference.

TABLE 2

| Relative values of maximum GIP-level elevation (10-minute value-initial value) | | | |
|---|---|---|---|
| | Maximum GIP-level elevation Average ± S.E. (pg/ml) | Significant difference from control group | Significant difference between sodium polyglutamate-administered group and potassium polyglutamate-administered group |
| Control group | 100.0 | — | — |
| Sodium polyglutamate (weight-average molecular weight: 9,000)-administered group | 102.9 ± 5.3 | N.S. | P < 0.05 |
| Potassium polyglutamate (weight-average molecular weight: 12,000)-administered group | 60.7 ± 4.9 | P < 0.05 | |

TABLE 2-continued

| Relative values of maximum GIP-level elevation (10-minute value-initial value) | | | |
|---|---|---|---|
| | Maximum GIP-level elevation Average ± S.E. (pg/ml) | Significant difference from control group | Significant difference between sodium polyglutamate-administered group and potassium polyglutamate-administered group |
| Sodium polyglutamate (weight-average molecular weight: 350,000)-administered group | 55.6 ± 3.1 | P < 0.05 | P < 0.05 |
| Potassium polyglutamate (weight-average molecular weight: 240,000)-administered group | 40.1 ± 2.8 | P < 0.05 | |

*) S.E.: Standard Error
*) N.S.: Not Significant

From the results of Table 2, it was found that the elevation of blood GIP level was not suppressed in the group to which the sodium polyglutamate of relatively low molecular weight having a weight-average molecular weight of 9,000 was administered. In contrast, the results showed that by increasing the weight-average molecular weight of the sodium polyglutamates to approximately 4-fold, namely, 350,000, the elevation of blood GIP level could be suppressed by about 45% (to about 55% with respect to the control) as compared to the control group. Further, the results also showed that by using the potassium polyglutamates having about one sixth weight-average molecular weight (weight-average molecular weight of 12,000), the elevation of blood GIP level could be suppressed by about 40% (to about 60% with respect to the control), which was almost equal suppression level to the above. Further, it was found that by increasing the weight-average molecular weight to 240,000, the elevation of blood GIP level could be suppressed by about 60% (to about 40% with respect to the control).

TABLE 3

| Relative values of maximum GIP-level elevation (10-minute value-initial value) | | | |
|---|---|---|---|
| | Maximum GIP-level elevation Average ± S.E. (pg/ml) | Significant difference from control group | Significant difference between sodium polyglutamate (weight-average molecular weight: 9,000)-administered group and potassium polyglutamate-administered group |
| Control group | 100.0 | — | — |
| Sodium polyglutamate (weight-average molecular weight: 9,000)-administered group | 102.8 ± 8.0 | N.S. | — |
| Potassium polyglutamate (weight-average molecular weight: 12,000)-administered group | 50.8 ± 4.1 | P < 0.05 | P < 0.05 |

TABLE 3-continued

| Relative values of maximum GIP-level elevation (10-minute value-initial value) | | | |
|---|---|---|---|
| | Maximum GIP-level elevation Average ± S.E. (pg/ml) | Significant difference from control group | Significant difference between sodium polyglutamate (weight-average molecular weight: 9,000)-administered group and potassium polyglutamate-administered group |
| Potassium polyglutamate (weight-average molecular weight: 6,000)-administered group | 58.2 ± 4.8 | P < 0.05 | P < 0.05 |

*) S.E.: Standard Error
*) N.S.: Not Significant

From the results of Table 3, it was found that the elevation of blood GIP level was not suppressed in the group to which the sodium polyglutamates of relatively low molecular weight having a weight-average molecular weight of 9,000 was administered. In contrast, the elevation of blood GIP level could be suppressed by about 50% when using the potassium polyglutamates having a weight-average molecular weight of 12,000, and the results of the above-mentioned Test Example 1 were reproduced.

In addition, the results showed that the potassium polyglutamates with lower molecular weight having a weight-average molecular weight of 6,000, also had the function of decreasing GIP to the level similar to that obtained by using potassium polyglutamates with a weight-average molecular weight of 12,000.

From the results of Test Example 2, it was found that the salts of polyglutamic acids had an effect of suppressing elevation of blood GIP level, and among these, potassium polyglutamates exerted a remarkably excellent effect of suppressing elevation of blood GIP level in the wide range of molecular weights.

As mentioned above, it is known that GIP has the effects of suppressing secretion of gastric acid, suppressing gastric motility, promoting uptake of glucose into adipocyte under the presence of insulin, and inducing insulin resistance. Thus, the above-mentioned potassium polyglutamates can be preferably used for promoting digestion, for preventing or reducing upset stomach, and for preventing or reducing obesity and insulin resistance by effectively suppressing elevation of blood GIP level.

Measurement and Evaluation of Insulin Level in Blood:

The blood collected by the heparin-treated hematocrit capillary was stored under ice-cooling until blood plasma separation, and centrifuged at 11,000 rpm for 5 minutes to give blood plasma. Blood insulin level in the obtained plasma was measured using an Insulin measurement kit (manufactured by Morinaga Institute of Biological Science, Inc., ELISA method).

The insulin levels in bloods up to 2 hours after the oral administration of the sample were measured. As a result, it was found that the blood insulin level became the maximum at 10 minutes after the administration. Thus, the difference (Δ value) between the maximum value (at 10 minutes after the administration) and the initial value (at the time of the initial blood sampling) of the blood insulin level was defined as the maximum insulin-level elevation, and Table 4 (results of Test Example 1) and Table 5 (results of Test Example 2) show the values when the value obtained from the control group defined as 100.

Further, the statistically-significant difference between the groups was also considered based on the obtained values of the maximum insulin-level elevation, and is shown in Table 4 and Table 5. When significance ($p<0.05$) was recognized by an analysis of variance, verifications were performed between the salts of polyglutamic acids-administered groups and the control group, and between the sodium salts-administered groups and similar molecular weight of the potassium salts-administered groups using a multiple comparison test (Bonferroni/Dunn method). From the obtained result, significance was judged with considering $p<0.05$ as a significant difference.

TABLE 4

| Relative values of maximum insulin-level elevation in mouse (10-minute value-initial value) | | | |
|---|---|---|---|
| | Maximum insulin-level elevation Average ± S.E. (pg/ml) | Significant difference from control group | Significant difference between sodium polyglutamate-administered group and potassium polyglutamate-administered group |
| Control group | 100.0 | — | — |
| Sodium polyglutamate (weight-average molecular weight: 9,000)-administered group | 103.3 ± 12.7 | N.S. | P < 0.05 |
| Potassium polyglutamate (weight-average molecular weight: 12,000)-administered group | 45.2 ± 5.2 | P < 0.05 | |
| Sodium polyglutamate (weight-average molecular weight: 350,000)-administered group | 86.2 ± 8.2 | N.S. | N.S. |
| Potassium polyglutamate (weight-average molecular weight of 240,000)-administered group | 78.3 ± 6.0 | P < 0.05 | |

*) S.E.: Standard Error
*) N.S.: Not Significant

From the results shown in Table 4, it was found that the sodium polyglutamates did not have a significant function of suppressing elevation of blood insulin level. In addition, it was also found that although the sodium polyglutamates-administered groups were not significantly different from the control group, those with a larger molecular weight increased an effect of suppressing elevation of blood insulin level. In contrast, the potassium polyglutamates showed an effect of suppressing elevation of blood insulin level regardless of their molecular weights.

The potassium polyglutamates with a weight-average molecular weight of 12,000, in particular, had an remarkably excellent effect in which the maximum insulin-level elevation in blood was suppressed by 50% or more (to about 45% with respect to the control).

TABLE 5

| Relative values of maximum insulin-level elevation in mouse (10-minute value-initial value) | | | |
|---|---|---|---|
| | Maximum insulin-level elevation Average ± S.E. (pg/ml) | Significant difference from control group | Significant difference between sodium polyglutamate (weight-average molecular weight: 9,000)-administered group and potassium polyglutamate-administered group |
| Control group | 100.0 | — | — |
| Sodium polyglutamate (weight-average molecular weight: 9,000)-administered group | 127.4 ± 20.0 | N.S. | — |
| Potassium polyglutamate (weight-average molecular weight: 12,000)-administered group | 76.3 ± 10.1 | P < 0.05 | P < 0.05 |
| Potassium polyglutamate (weight-average molecular weight: 6,000)-administered group | 88.6 ± 10.0 | P < 0.05 | P < 0.05 |

*) S.E.: Standard Error
*) N.S.: Not Significant

It was found that when using the sodium polyglutamates with a weight-average molecular weight of about 9,000, an effect of suppressing elevation of blood insulin level was not recognized, whereas the potassium polyglutamates with a weight-average molecular weight of 12,000 remarkably suppressed the maximum insulin-level elevation in blood.

It was further revealed that the potassium polyglutamates with a low molecular weight having a weight-average molecular weight of 6,000 had an effect of suppressing elevation of an insulin level similar to that obtained when using potassium polyglutamates having a weight-average molecular weight of 12,000.

From the results of Test Examples 1 and 2, it was also found that when using potassium polyglutamates, the molecular weight of the potassium polyglutamates became lower, surprisingly the effect of suppressing elevation of blood insulin level became higher, whereas when using sodium polyglutamates, the molecular weight of the sodium polyglutamates became larger, the function of suppressing elevation of blood insulin level tended to became higher. The viscosity of the salts of polyglutamic acids become lower as decreasing the molecular weight of the salts of polyglutamic acids. Thus, when potassium polyglutamates with low molecular weight can be used, handling in the production process be easy. In addition, when the agent for suppressing elevation of blood insulin level of the present invention is formed into an oral liquid agent, there is an advantage to be able to obtain a liquid agent excellent in feeling of the throat, slimy feeling, ease of swallowing and the like during ingestion, by using potassium polyglutamates with low molecular weight.

As mentioned above, it is known that excessive elevation of blood insulin level leads to insulin resistance, eventually causes obesity and diabetes mellitus. Thus, the potassium polyglutamates can be preferably used for preventing or reducing obesity and diabetes mellitus by suppressing insulin secretion after meal ingestion.

Measurement and Evaluation of Triglyceride Level in Blood:

The blood collected by the heparin-treated hematocrit capillary was stored under ice-cooling until plasma separation, and centrifuged at 11,000 rpm for 5 minutes to give plasma. Blood triglyceride level in the obtained plasma was measured by using triglyceride E-test Wako (manufactured by Wako Pure Chemical Industries, Ltd., GPO-DADS method).

Based on the results of the measurement of the triglyceride levels in bloods up to 2 hours after the oral administration of the sample, the difference (Δ value) between the maximum value and the initial value (at the time of the initial blood sampling) of the blood triglyceride level was defined as the maximum triglyceride-level elevation, and Table 6 (results of Test Example 1) and Table 7 (results of Test Example 2) show the values when the value obtained from the control group defined as 100.

Further, the statistically-significant difference between the groups was also considered based on the obtained values of the maximum triglyceride-level elevation, and is shown in Table 6 and Table 7. Verifications were performed between the salts of polyglutamic acids-administered groups and the control group, and between the sodium salts-administered groups and similar molecular weight of the potassium salts-administered groups using a multiple comparison test (Bonferroni/Dunn method). From the obtained result, significance was judged with considering $p<0.05$ as a significant difference.

TABLE 6

Relative values of maximum triglyceride-level elevation in mouse (maximum value-initial value)

| | Maximum triglyceride-level elevation Average ± S.E. (mg/dl) | Significant difference from control group | Significant difference between sodium polyglutamate-administered group and potassium polyglutamate-administered group |
|---|---|---|---|
| Control group | 100.0 | — | — |
| Sodium polyglutamate (weight-average molecular weight: 9,000)-administered group | −47.3 ± 30.3 | P < 0.05 | P < 0.05 |
| Potassium polyglutamate (weight-average molecular weight: 12,000)-administered group | −144.4 ± 33.2 | P < 0.05 | |
| Sodium polyglutamate (weight-average molecular weight: 350,000)-administered group | 15.1 ± 16.6 | P < 0.05 | P < 0.05 |
| Potassium polyglutamate (weight-average molecular weight: 240,000)-administered group | −59.5 ± 11.9 | P < 0.05 | |

*) S.E.: Standard Error

*) N.S.: Not Significant

From the results of Table 6, it was found that in all cases in which the salts of polyglutamic acids were administered, the maximum triglyceride-level elevation could be effectively suppressed or lowered.

In addition, when potassium polyglutamates were administered, further remarkable effect of lowering blood triglyceride level was recognized. This can be understood from that a lowering effect obtained by using the potassium polyglutamates with a weight-average molecular weight of 12,000 exceeding suppressing effect of the maximum triglyceride-level elevation was more excellent than those obtained by using sodium polyglutamates with a weight-average molecular weight of 9,000.

TABLE 7

Relative values of maximum triglyceride-level elevation (maximum value-initial value)

| | Maximum triglyceride-level elevation Average ± S.E. (mg/dl) | Significant difference from control group | Significant difference between sodium polyglutamate (weight-average molecular weight: 9,000)-administered group and potassium polyglutamate-administered group |
|---|---|---|---|
| Control group | 100.0 | — | — |
| Sodium polyglutamate (weight-average molecular weight: 9,000)-administered group | −31.9 ± 22.1 | N.S. | — |
| Potassium polyglutamate (weight-average molecular weight: 12,000)-administered group | −181.3 ± 40.6 | P < 0.05 | P < 0.05 |
| Potassium polyglutamate (weight-average molecular weight: 6,000)-administered group | −144.5 ± 17.4 | P < 0.05 | P < 0.05 |

*) S.E.: Standard Error

*) N.S.: Not Significant

From the results of Table 7, it was reconfirmed that when the potassium polyglutamates were administered, a remarkably excellent effect of lowering blood triglyceride level was recognized as compared to the case where the sodium polyglutamates were administered.

In addition, it was ascertained that the effect of lowering blood triglyceride level exerted by the potassium polyglutamates with a weight-average molecular weight of 6,000 was the same level as that obtained by using potassium polyglutamates with a weight-average molecular weight of 12,000.

As mentioned above, it is known that elevation of blood triglyceride level causes hyperlipidemia and eventually arteriosclerosis. Thus, the above potassium polyglutamates can be preferably used for preventing or reducing hyperlipidemia and arteriosclerosis by effectively lowering blood triglyceride level after meal ingestion.

Measurement and Evaluation of Blood Glucose Level:

Using blood collected by a heparin-treated hematocrit capillary, blood glucose levels were immediately measured using a simple blood sugar monitoring meter ACCU-CHEK (trade name, manufactured by Roche Diagnostics K.K.).

The blood glucose level up to 2 hours after the oral administration of the sample was measured. As a result, it was found that the blood glucose level became the maximum at 10 minutes after the administration. Therefore, the difference (Δ value) between the maximum value (at 10 minutes after the administration) and the initial value (at the time of the initial blood sampling) of the blood glucose level was defined as the maximum blood glucose-level elevation, and Table 8 show the values when the value obtained from the control group defined as 100.

The statistically-significant difference between the groups was also studied based on the obtained values of the maximum blood glucose-level elevation, and is shown in Table 8. When significance ($p<0.05$) was recognized by an analysis of variance, verifications were performed between the salts of polyglutamic acids-administered groups and the control group, and between the sodium salts-administered groups and similar molecular weight of the potassium salts-administered groups using a multiple comparison test (Bonferroni/Dunn method). From the obtained result, significance was judged with considering $p<0.05$ as a significant difference.

TABLE 8

Relative values of maximum blood glucose-level elevation in mouse (10-minute value-initial value)

| | Maximum blood glucose-level elevation Average ± S.E. (mg/dL) | Significant difference from control group | Significant difference between sodium polyglutamate-administered group and potassium polyglutamate-administered group |
|---|---|---|---|
| Control group | 100 | — | — |
| Sodium polyglutamate (weight-average molecular weight: 9,000)-administered group | 99 ± 4 | N.S. | P < 0.05 |
| Potassium polyglutamate (weight-average molecular weight: 12,000)-administered group | 86 ± 3 | P < 0.05 | |
| Sodium polyglutamate (weight-average molecular weight: 350,000)-administered group | 104 ± 3 | N.S. | P < 0.05 |
| Potassium polyglutamate (weight-average molecular weight: 240,000)-administered group | 88 ± 4 | P < 0.05 | |

*) S.E.: Standard Error
*) N.S.: Not Significant

From the results of Table 8, it was found that the sodium polyglutamates did not have the function of suppressing elevation of blood glucose level regardless of their molecular weights. In contrast, in the groups to which the potassium polyglutamates were administered, the elevation of blood glucose level was significantly suppressed as compared to both the control group and the sodium salts-administered groups. From the above results, it was found that by employing potassium polyglutamates as active ingredients of the agent for suppressing elevation of blood glucose level, a remarkable effect of suppressing elevation of blood glucose level, which could not be obtained using other polyglutamic acid salts, could be obtained.

As mentioned above, it is known that rapid elevation of blood glucose level after meal ingestion leads to insulin resistance, eventually causes diabetes mellitus, obesity and arteriosclerosis. Thus, the above potassium polyglutamates can be preferably used for preventing or reducing diabetes mellitus, obesity and arteriosclerosis by effectively suppressing rapid elevation of blood glucose level.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2011-004313, Patent Application No. 2011-004314, Patent Application No. 2011-004315 and Patent Application No. 2011-004316 filed in Japan on Jan. 12, 2011, which are entirely herein incorporated by reference.

What is claimed is:

1. A method for suppressing elevation of blood GIP level, the method comprising administering a potassium polyglutamate to a subject, wherein the potassium polyglutamate suppresses elevation of blood GIP level, and wherein the weight-average molecular weight of the potassium polyglutamate is from 500 to 5,000,000.

2. The method according to claim 1, wherein the elevation of blood GIP level is elevation of blood GIP level after meal ingestion.

3. The method according to claim 1, wherein the potassium polyglutamate has a polyglutamic-acid structure in which 50% or more of hydrogen atoms in carboxyl groups are substituted with potassium.

4. The method according to claim 1, wherein the dosage of the potassium polyglutamate is from 0.001 to 1.0 g/kg body weight per day.

5. The method according to claim 1, wherein the potassium polyglutamate is administered to the subject during a period from 30 minutes before starting meal ingestion to 30 minutes after finishing the meal ingestion.

6. The method according to claim 1, wherein the subject is a obese person or a person with metabolic syndrome, or a potential patient thereof.

7. The method according to claim 2, wherein the elevation of blood GIP level after meal ingestion is elevation of blood GIP level in a period from 0 min to 6 hours after finishing the meal ingestion.

8. The method according to claim 1, wherein the administering is by gastrointestinal administration, intraperitoneal administration, intravascular administration, intradermal administration, or subcutaneous administration.

9. The method according to claim 8, wherein the administering is by gastrointestinal administration.

10. The method according to claim 1, wherein the administering is conducted by ingesting food, a medicinal product or pet food containing the potassium polyglutamate as an active ingredient.

* * * * *